United States Patent [19]

Kurihara et al.

[11] Patent Number: 5,382,380

[45] Date of Patent: Jan. 17, 1995

[54] P-TERPHENYL DERIVATIVES AND LIQUID CRYSTALLINE COMPOSITIONS

[75] Inventors: Makoto Kurihara; Hiromi Inoue; Atsushi Sugiura; Kenji Suzuki; Tsunenori Fujii, all of Soka, Japan

[73] Assignee: Kanto Kagaku Kabushiki Kaisha, Tokyo, Japan

[21] Appl. No.: 892,735

[22] Filed: Jun. 1, 1992

Related U.S. Application Data

[63] Continuation of Ser. No. 397,907, Aug. 24, 1989, abandoned.

[30] Foreign Application Priority Data

Sep. 1, 1988 [JP] Japan .................. 63-216294

[51] Int. Cl.$^6$ .................. C09K 19/12; C07C 69/76; C07C 41/00
[52] U.S. Cl. .................. 252/299.66; 252/299.01; 252/299.61; 560/59; 560/64; 560/65; 560/141; 568/631; 568/642; 568/661
[58] Field of Search .................. 252/299.01, 299.66, 252/299.61; 560/59, 64, 65, 141; 568/631, 642, 661

[56] References Cited

U.S. PATENT DOCUMENTS

| | | | |
|---|---|---|---|
| 4,594,465 | 6/1986 | Kam Ming Chan et al. | 252/299.66 |
| 4,654,162 | 3/1987 | Sugimori et al. | 252/299.66 |
| 4,753,752 | 6/1988 | Raynes et al. | 252/299.66 |
| 4,780,240 | 10/1988 | Emoto et al. | 252/299.66 |
| 4,780,241 | 10/1988 | Furukawa et al. | 252/299.66 |
| 4,808,333 | 2/1989 | Huynh-Ba et al. | 252/299.66 |
| 4,943,387 | 7/1990 | Furukawa et al. | 252/299.66 |

FOREIGN PATENT DOCUMENTS

| | | |
|---|---|---|
| 0132377 | 1/1985 | European Pat. Off. |
| 0174191 | 3/1986 | European Pat. Off. |
| 0277815 | 8/1988 | European Pat. Off. |
| 0278665 | 8/1988 | European Pat. Off. |
| 0315701 | 5/1989 | European Pat. Off. |
| 2200912A | 8/1988 | United Kingdom |

OTHER PUBLICATIONS

Clark et al., Appl. Phys. Lett. 36(11), 1 Jun. 1980, pp. 899–901.

Meyer et al., Le Journal de Physique–Lettres, Tome 36, Mars. 1975, P. L–69.

Chan, et al., Mol. Cryst. Liq. Cryst., 123, 185–204 (1985).

*Primary Examiner*—Philip Tucker
*Attorney, Agent, or Firm*—Birch, Stewart, Kolasch & Birch

[57] ABSTRACT

New p-terphenyl derivatives useful as components for preparing practical ferroelectric liquid crystalline compositions and excellent in chemical stability, as well as liquid crystalline compositions containing at least one of the p-terphenyl derivatives.

14 Claims, No Drawings

P-TERPHENYL DERIVATIVES AND LIQUID CRYSTALLINE COMPOSITIONS

This application is a continuation of application Ser. No. 07/397.907 filed on Aug. 24, 1989, now abandoned.

DETAILED DESCRIPTION OF THE INVENTION

1. Technical Field

The present invention relates to new liquid crystalline compounds as well as liquid crystalline compositions containing at least one of the liquid crystalline compounds. More particularly, the present invention relates to ferroelectric liquid crystals and to new p-terphenyl derivatives which are useful as components for preparing practical ferroelectric liquid crystalline compositions and excellent in chemical stability as well as liquid crystalline compositions containing at least one of the p-terphenyl derivatives.

2. Background Art

Liquid crystal display elements are widely used as display elements for watches, electronic desk-top computers, personal word processors, pocket-size TV sets, etc. They are, on one hand, characterized by such beneficial characteristics as no eyestrain because of their passive device, low electric power consumption, a thin structure etc., but on the other hand undergo restrictions in their practical applications because of slow response and lack of memory effect. In an attempt to expand their areas of application there have been provided, for example, the super twisted nematic (STN) display system, which is an improvement of the twisted nematic (TN) display system. These systems, however, are not sufficient for large screen or graphic display use. Various studies have therefore been made of liquid crystal display elements which can supersede them. One such display system [N. A. Clark et al., Applied Phys. lett., 36, 899 (1980)] utilizes ferroelectric liquid crystals [R. B. Meyer et al., Physique, 36 L-69 (1975)]. Because of its advantageous characteristics such as fast response, which is 100 times as fast as that of conventional systems, and memory effect, it is expected to expand areas of application of liquid crystal display elements. The term "ferroelectric liquid crystal" is used to mean a series of smectic liquid crystals whose molecular longitudinal axis is at a certain angle to the normal of the layer, but in practice the chiral smectic C (SmC*) phase is utilized.

In practice, ferroelectric liquid crystals for display elements are used as a liquid crystalline composition comprising a number of ferroelectric liquid crystalline compounds or prepared by blending such compound(s) and one or more compounds having the smectic C (SmC) phase. As is the case with the preparation of nematic liquid crystal display elements, mixing of a number of components is required in this case if different properties required for actual use such as operating temperature range, response time, helical pitch, chemical stability and so on are to be satisfied.

Ferroelectric liquid crystalline compositions have not been put to actual use yet, it therefore being desired that a variety of compounds useful as components for such compositions be developed. In particular, there has been need for the development of substances which show the SmC phase over a wide temperature range, and which have the SmC* phase and an adequate spontaneous polarization value. The object of the present invention is to provide new substances which satisfy such need.

Known p-terphenyl compounds of analogous structure are disclosed, for example, in EP-013277, GB-2200912 and Mol. Cryst. Liq. Cryst., 1985, Vol. 123, pp. 185-204.

The present invention provides substances which have a wider temperature range for the SmC or SmC* phase than these known compounds, as well as substances which have SmC* phase and an adequate spontaneous polarization value.

DISCLOSURE OF THE INVENTION

The present inventors designed, synthesized, evaluated and extensively studied compounds of different new structures, paying particular attention to their temperature range in which a ferroelectric property is shown. As a result the inventors have succeeded in providing new compounds which have a wide temperature range for the SmC* or SmC phase as well as chemical stability and excellent response time.

The present invention thus provides p-terphenyl derivatives of the general formula

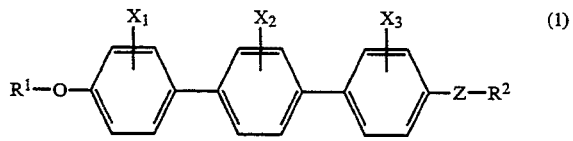 (1)

wherein $R^1$ is an asymmetric carbon-containing alkyl group having 4-18 carbon atoms; $R^2$ is a straight chain alkyl group having 1-18 carbon atoms; Z is a single bond, O, COO or OCO; and $X_1$, $X_2$ and $X_3$ are all hydrogen atoms or any one of them is a fluorine atom and the others are hydrogen atoms, as well as liquid crystalline compositions containing at least one of these derivatives.

The new compounds according to the present invention, even when used individually, exhibit the SmC or SmC* phase over a wide temperature range. Ferroelectric liquid crystalline compositions with an even wider temperature range for the SmC* phase, however, are obtainable by preparing mixtures of these compounds or mixtures of one or more such compounds with one or more other liquid crystalline compounds or compositions.

Accordingly, the p-terphenyl derivatives according to the present invention are useful substances utilizable as components for preparing ferroelectric liquid crystalline compositions for use in ferroelectric liquid crystal display elements.

Processes for their preparation will be described below in detail by showing synthetic routes, working examples etc. The phase transition temperature of synthesized compounds will be affected by the measuring instrument or method or the purity of the substance, it thus being to be understood that measured values will more or less vary.

The new p-terphenyl derivatives according to the present invention can be synthesized through a variety of routes, for example according to the routes schematized below.

Schematized synthetic route example I
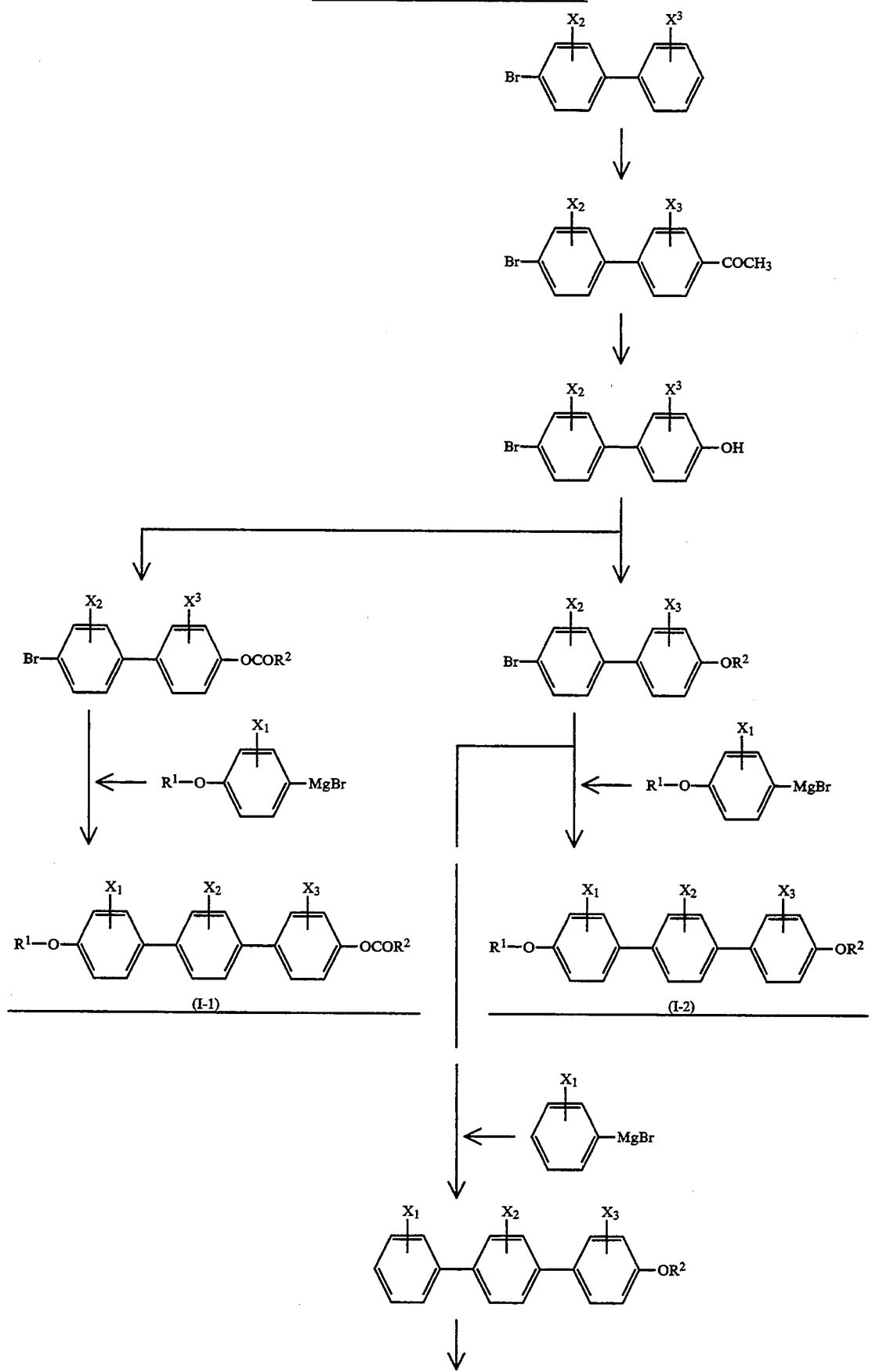

-continued
Schematized synthetic route example I
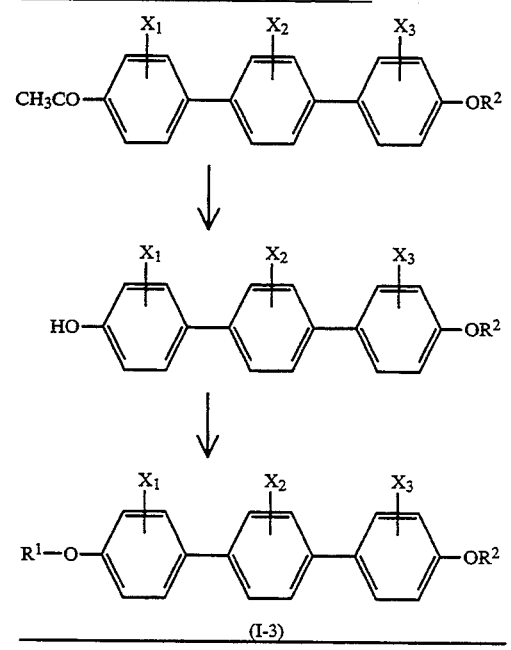
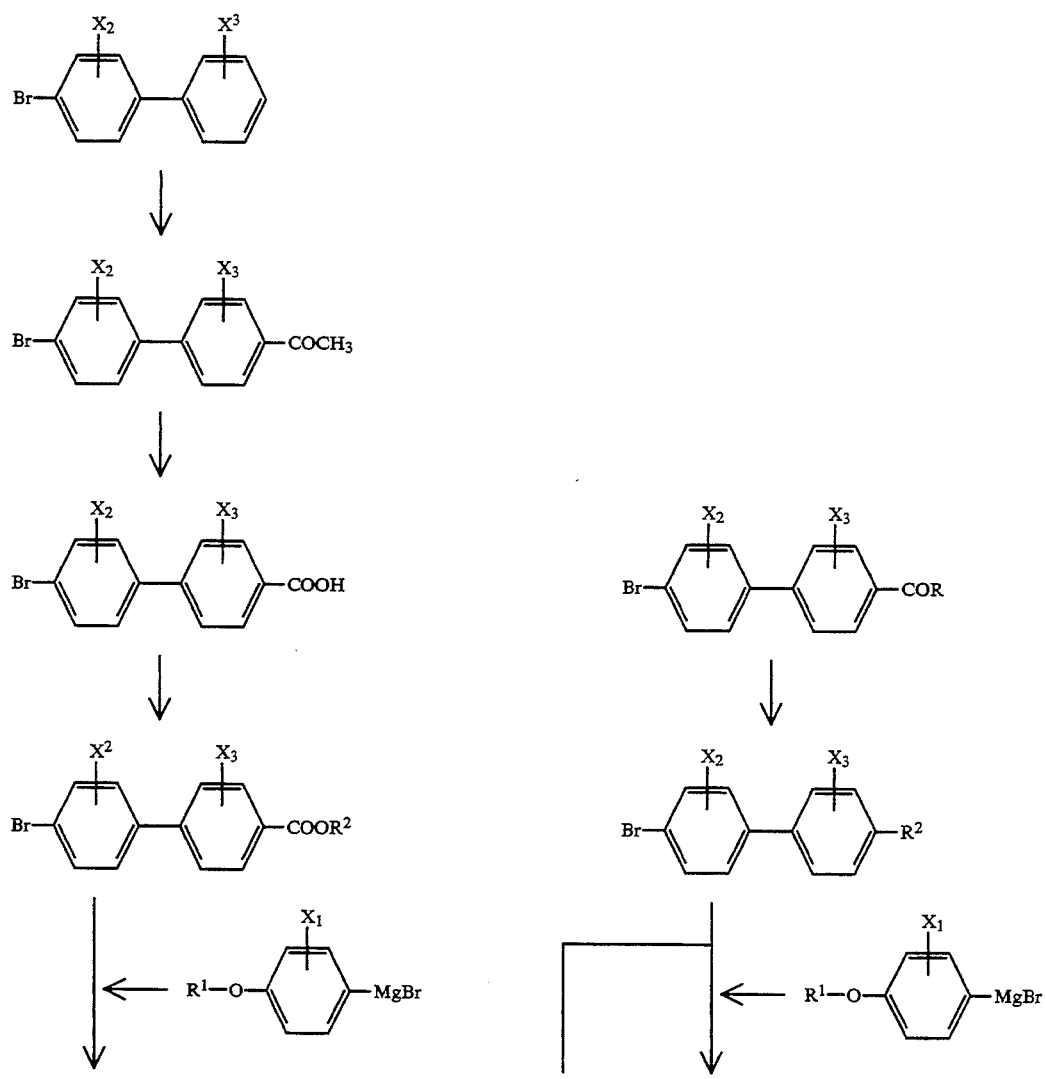

-continued
Schematized synthetic route example I
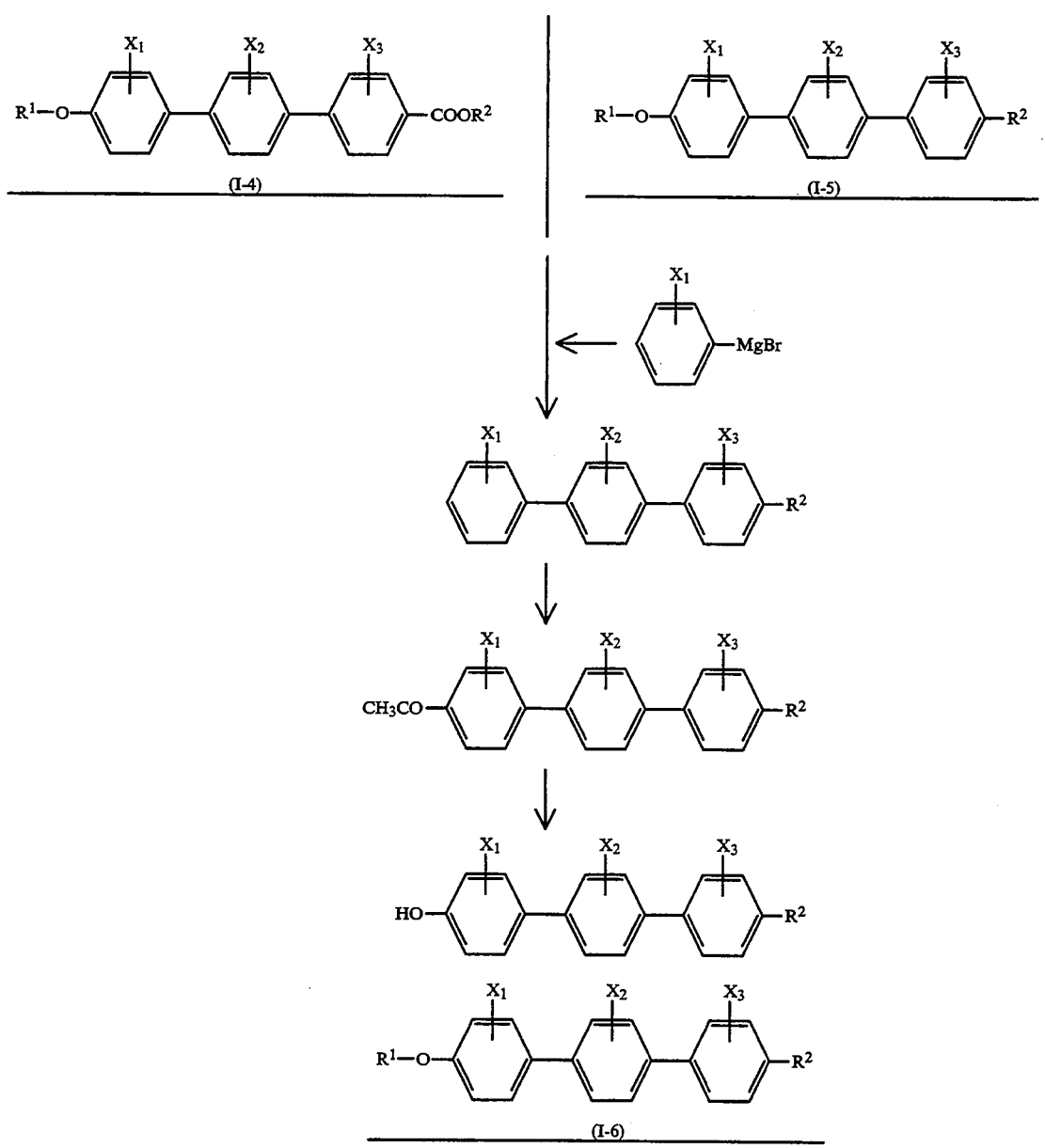
Schematized synthetic route example II
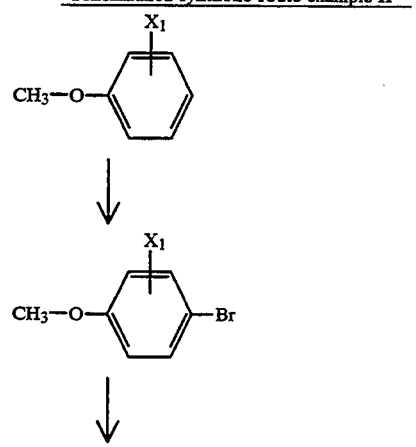

-continued
Schematized synthetic route example II

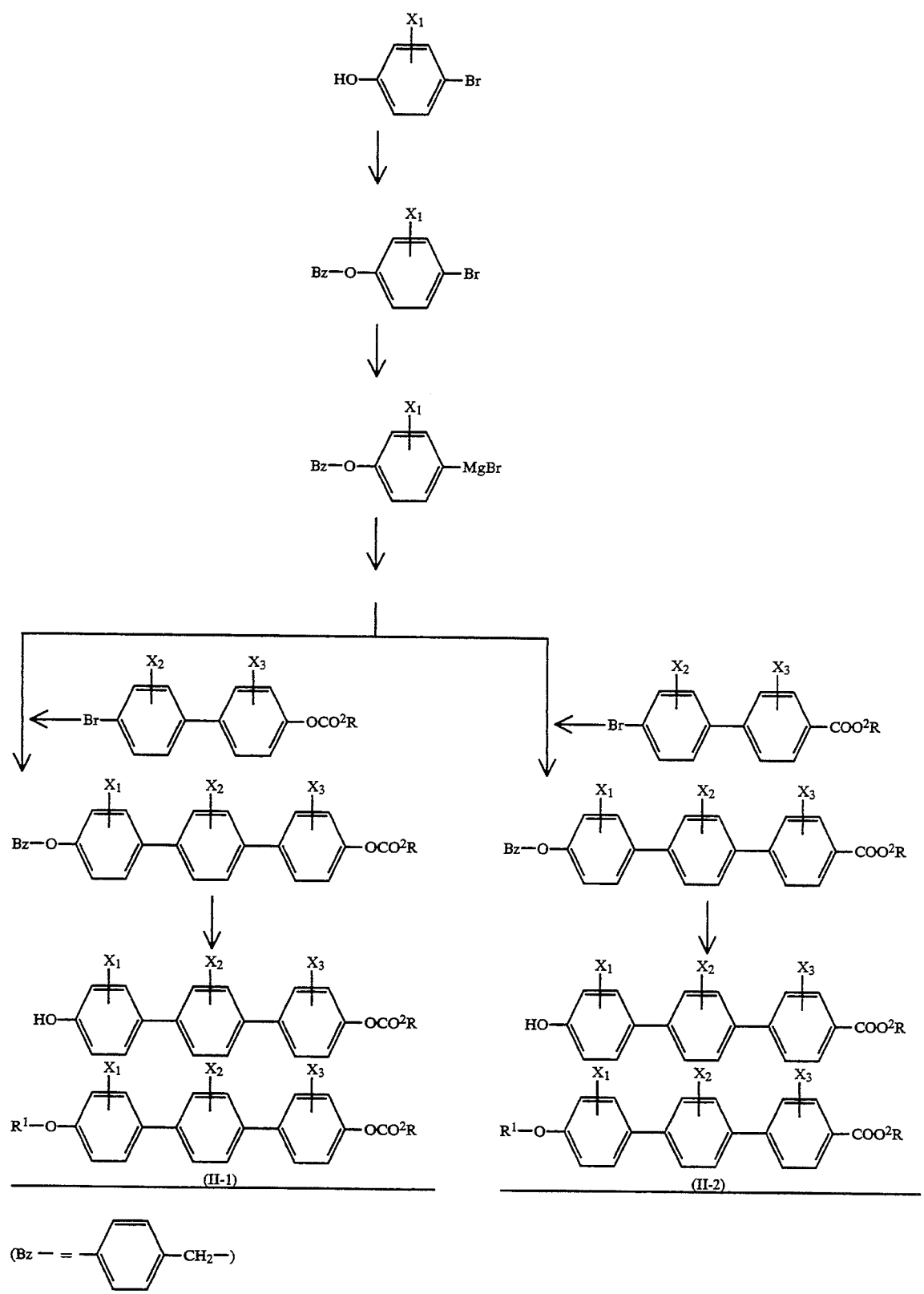

(Bz— = —⟨phenyl⟩—CH₂—)

The schematized synthetic routes will now be described below.

4-Alkyloxy-4'''-alkyloxy-p-terphenyls and derivatives thereof (I-2) can be synthesized by subjecting 4-bromobiphenyl or its derivative as starting material to acetylation, Baeyer-Villiger oxidation, hydrolysis and etherification and then to cross-coupling reaction with a Grignard reagent prepared from a 4-alkyloxybromobenzene or its derivative. 4-Alkyloxy-4"-alkyl-p-terphenyls and derivatives thereof (I-6) can be synthesized by subjecting 4-bromobiphenyl or its derivative as starting material to acylation, reduction, cross-coupling reaction with a Grignard reagent prepared from bromobenzene or its derivative, acetylation, Baeyer-Villiger oxidation and etherification. 4-Alkyloxy-4"-alkyloxycarbonyl-p-terphenyls and derivatives thereof (II-2) can be synthesized by subjecting anisole or its derivative as starting material to bromination, ether-cleavage and benzyl-etherification followed by conversion into a Grignard reagent, which is then subjected to cross-coupling reaction with a 4-bromo-4'-alkyloxycarbonyl-biphenyl or its derivative followed by ether-cleavage and reetherification. The other end compounds (I-1, I-2, I-4, I-5 and II-1) shown in "Schematized synthetic route examples" can be synthesized by appropriately combining the above mentioned reactions in respective processes.

In the examples given below, the notations and abbreviations are used to mean the following:
GLC : gass chromatography
HPLC : high performance liquid chromatography
IR : infra-red rays absorption spectroscopy
Mass : mass spectrometry
m.p. : melting point
C : crystals
Sx : unidentified smectic phase
SB : smectic B phase
SmC, Sc : smectic C phase
SmC*, Sc* : chiral smectic C phase
SA : smectic A phase
Ne : nematic phase
Ch : cholesteric phase
I : isotropic liquid
? : temperature being indefinite

EXAMPLE 1

(a) Synthesis of

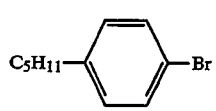

A reaction vessel was charged with 100 g of 4-pentylaniline and 600 ml of water, and 80 g of concentrated sulfuric acid was added dropwise with ice water cooling and stirring. A solution of 43 g of sodium nitrite in 80 ml of water was then added dropwise and the reaction was carried out at the same temperature for 2 hours with stirring whereby a diazonium salt solution was prepared. Another reaction vessel was charged with 38.5 g of cupric sulfate pentahydrate (CuSO₄.5H₂O ), 12.2g of copper powder, 70 g of sodium bromide and 600 ml of water. To the mixture were added at room temperature with stirring 18.5 g of concentrated sulfuric acid and then 4.5 g of sodium sulfite heptahydrate. The temperature of the resultant temperature was allowed to rise, and the previously prepared diazonium salt solution was added dropwise over a period of 1 hour under reflux with stirring, whereafter the mixture was subjected to reaction for a further period of 1 hour. The reaction liquid was cooled and then extracted with 1 l of hexane added. The resultant hexane solution was washed successively with water, aqueous caustic soda and water and then dried over Glauber's salt. The hexane was distilled off and the residue was distilled under reduced pressure to obtain 61.5 g (44%) of 4-pentyl-bromobenzene (b.p. 135°–142° C./ 15–17 mmHg).
GLC 96%

(b) Synthesis of

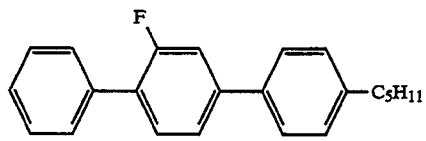

A reaction vessel was charged with 3.3 g of magnesium powder and a small piece of iodine. A small portion of a solution of 22.7 g of 4-pentyl-bromobenzene obtained in (a) above in 50 ml of tetrahydrofuran (THF) was added thereto, and the resultant mixture was heated with stirring. After foaming indicating the initiation of the reaction, the remainder of the above mentioned THF solution was added dropwise in such a manner that the resultant mixture was kept refluxed. After the dropwise addition, the mixture was refluxed with stirring for a further period of 2 hours to prepare a Grignard reagent.

Another reaction vessel was charged with 0.5 g of dichlorobistriphenylphosphinepalladium [Cl₂Pd(PPh₃)₂] and 30 ml of THF. To the mixture was added 1.5 ml of a 1M solution of diisobutyl aluminium hydride [(iso-C₄H₉)₂AlH] in hexane. A solution of 19.5 g of 4-bromo-2-fluorobiphenyl in 90 ml of THF was then added at room temperature with stirring. After the temperature of the mixture rose to 60° C., the previously prepared Grignard reagent was added dropwise. After the dropwise addition, the mixture was allowed to ripe for 2 hours. The reaction liquid was poured into 400 ml of a mixture of hydrochloric acid and ice water, and the resultant mixture was extracted with benzene and the extract was washed with a saturated aqueous solution of edible salt until the washings became neutral and dried over Glauber's salt. The resultant benzene solution was distilled to evaporate off the solvents, and the residue was distilled under reduced pressure to obtain a fraction (b.p. 198°–208° C./0.6 mmHg), which was then recrystallized from hexane to obtain 12.0 g (48.5%) of 4-pentyl-3'-fluoro-p-terphenyl.
GLC 98.0%

(c) Synthesis of

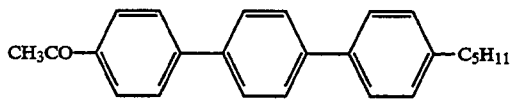

A reaction vessel was charged with 30 ml of methylene chloride and 7 g of anhydrous aluminum chloride. To the mixture was added, with stirring at a temperature not higher than 0° C., 5.6 g of acetyl chloride and was then added dropwise a solution of 8.33 g of 4-pentyl-3'-fluoro-p-terphenyl obtained in (b) above in 50 ml of methylene chloride. The resultant mixture was reacted at the same temperature for 2 hours with stirring. The reaction liquid was poured into cold diluted hydrochloric acid and the mixture was extracted with benzene and the extract was washed successively with a saturated aqueous solution of edible salt, an aqueous solution of sodium hydrogen carbonate and a saturated aqueous solution of edible salt and then dried over Glauber's salt. The solvents were distilled off and the residue was recrystallized from acetone to obtain 6.45 g (68.4%) of 4-acetyl-2'-fluoro-4"-pentyl-p-terphenyl.

HPLC 97%

(d) Synthesis of

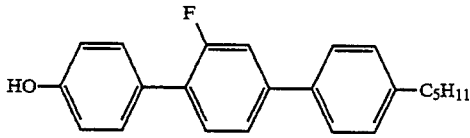

A reaction vessel was charged with 6 g of 4-acetyl-2'-fluoro-4"-pentyl-p-terphenyl obtained in (c) above and 50 ml of methylene chloride. To the mixture were added successively at room temperature with stirring 50 ml of 88% formic acid, 25 ml of acetic anhydride and 0.1 ml of concentrated sulfuric acid, and was then added dropwise at 14° C. 7 ml of 35% aqueous hydrogen peroxide. After the dropwise addition the mixture was reacted at 40° C. for 24 hours with stirring and the reaction liquid was then poured into ice water. The mixture was extracted with benzene and the extract was washed with diluted hydrochloric acid and then with an aqueous solution of edible salt and dried over Glauber's salt. The resultant benzene solution was distilled to evaporate off the benzene. A reaction vessel was charged with the residue, 300 ml of ethyl alcohol and 55 ml of a 30% aqueous solution of caustic potash, and the resultant mixture was refluxed with stirring for 8 hours. The reaction liquid was poured into cold diluted hydrochloric acid and the mixture was extracted with benzene. The extract was washed with an aqueous solution of edible salt and then dried over Glauber's salt. The benzene was distilled off and the resultant residue was purified by way of column chromatography on silica gel (eluent: chloroform) and then recrystallized from methanol to obtain 1.8 g (32.4%) of 4-hydroxy-2'-fluoro-4"-pentyl-p-terphenyl.

HPLC 99.5%

(e) Synthesis of

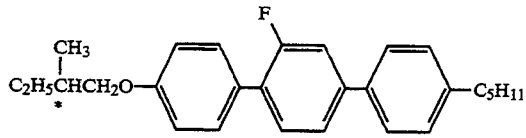

A reaction vessel was charged with 0.6 g of 4-hydroxy-2'-fluoro-4"-pentyl-p-terphenyl obtained in (d) above, 1 g of (S)-2-methylbutyl bromide, 0.8 g of potassium carbonate and 10 ml of 2-butanone (MEK), and the mixture was reacted under reflux and agitation for 16 hours. The reaction liquid was poured into diluted hydrochloric acid and the mixture was extracted with benzene. The extract was washed with water and dried over Glauber's salt. The solvents were then distilled off and the residue was purified by way of column chromatography on silica gel (eluent: hexane/benzene=4: 1) to obtain 0.3 g (41.7%) of (S)-4-(2-methylbutyl)oxy-2'-fluoro-4"-pentyl-p-terphenyl.

The purity of this product was at least 98% by HPLC. The thus obtained substance was confirmed to be the end product in view of its measurement by IR and its molecular ion peak found at 404 by Mass and in view of the starting materials used.

This product was inserted into a Mettler hot stage FP-82 and its phase transition was observed under a polarization microscope. A result of the observation is shown in Table 1.

EXAMPLE 2

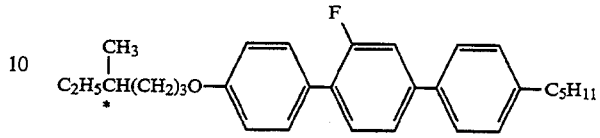

Except that 0.36 g of (S)-4-methylhexyl bromide was used in place of 1 g of (S)-2-methylbutyl bromide used in Example 1 (e), the operation was performed in the same manner as in Example 1 and the resultant product was recrystallized from acetone to obtain 0.48 g (61.9%) of (S)-4-(4-methylhexyl)oxy-2'-fluoro-4"-pentyl-p-terphenyl.

The purity of the product was at least 99% by HPLC. The thus obtained substance was confirmed to be the end product in view of its measurement by IR and its molecular ion peak found at 432 by Mass and in view of the starting materials used.

This product was inserted into a Mettler hot stage FP-82 and its phase transition was observed under a polarization microscope. A result of the observation is shown in Table 1.

EXAMPLE 3

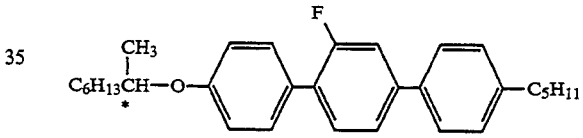

Except that 2.0 g of (S)-1-methylheptyl tosylate was used in place of 1 g of (S)-2-methylbutyl bromide used in Example 1 (e), the operation was performed in the same manner as in Example 1 to obtain 0.5 g (62.5%) of (R)-4-(1-methylheptyl)oxy-2'-fluoro-4"-pentyl-p-terphenyl.

The purity of this product was at least 99% by HPLC. The thus obtained substance was confirmed to be the end product in view of its measurement by IR and its molecular ion peak found at 446 by Mass and in view of the starting materials used.

This product was inserted into a Mettler hot stage FP-82 and its phase transition was observed under a polarization microscope. A result of the observation is shown in Table 1.

EXAMPLE 4

(a) Synthesis of

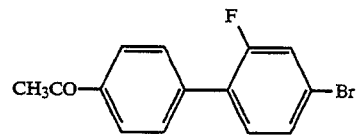

A reaction vessel was charged with 113 g of anhydrous aluminum chloride and 600 ml of methylene chloride. To the mixture was added dropwise 113 g of acetyl chloride with stirring at a temperature not higher than 0° C., and was then added dropwise a solution of 100 g of 4-bromo-2-fluoro-biphenyl in 400 ml of methylene chloride. The mixture was reacted with stirring for 7 hours while gradually bringing it back to room temperature. The reaction liquid was poured into ice and diluted hydrochloric acid. The methylene chloride layer was washed successively with water, an aqueous solution of sodium hydrogen carbonate and water, and then dried over Glauber's salt. The solvent was then distilled off and the residue was recrystallized from acetone to give 96 g (82.2%) of 4-acetyl-2'-fluoro-4'-bromobiphenyl.

GLC 100%

(b) Synthesis of

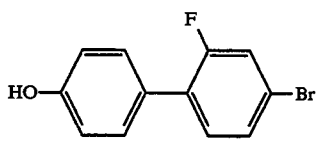

A reaction vessel was charged with 65 g of 4-acetyl-2'-fluoro-4'-bromobiphenyl obtained in (a) above and 300 ml of methylene chloride. To the mixture was added dropwise 500 ml of 88% formic acid and 480 ml of acetic anhydride with stirring at 10° C. and was then added 1.5 ml of concentrated sulfuric acid. To the resultant mixture was added dropwise 150 ml of 35% aqueous hydrogen peroxide over a period of 3 hours. After the dropwise addition, the mixture was gradually warmed up to 45°–50° C. at which temperature it was reacted with stirring for 30 hours. The reaction liquid was poured into ice water and the mixture was extracted with benzene. The extract was washed with an aqueous solution of sodium hydrogen carbonate and then with water, and dried over Glauber's salt. The solvents were distilled off and the residue obtained and 2 l of ethyl alcohol were charged into another reaction vessel. To the mixture was added a 25% aqueous solution caustic potash and the resultant mixture was refluxed with stirring for 8 hours. The reaction liquid was poured into ice and diluted hydrochloric acid and the mixture was extracted with benzene. The extract was washed with an aqueous solution edible salt and dried over Glauber's salt. The solvent was distilled off and the residue was purified by way of column chromatography on silica gel using benzene as eluent to obtain 28.1 g (47.5%) of 4-hydroxy-2'-fluoro-4'-bromobiphenyl.

(c) Synthesis of

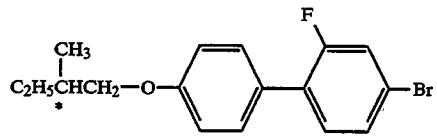

A reaction vessel was charged with 5 g of 4-hydroxy-2'-fluoro-4'-bromobiphenyl obtained in (b) above, 6.8 g of (S)-2-methylbutyl bromide, 4 g of potassium carbonate and 50 ml of 2-butanone (MEK), and the mixture was reacted under reflux and agitation for 8 hours. The reaction liquid was poured into diluted hydrochloric acid and the mixture was extracted with benzene. The extract was washed with water and dried over Glauber's salt and the solvents were distilled off. The residue was distilled in a glass tube oven (GTO) to obtain a fraction (GTO-set temperature: 140°C./0.2 mmHg), which was then purified by way of column chromatography on silica gel using hexane:benzene (=4:1) as eluent to obtain 4.54 g (72.0%) of (S)-4-(2-methylbutyl)oxy-2'-fluoro-4'-bromobiphenyl.

TLC monospot (d) Synthesis of

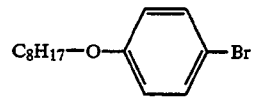

A reaction vessel was charged with 22.3 g of octyl bromide, 20 g of p-bromophenol, 33.3 g of potassium carbonate and 200 ml of 2-butanone (MEK), and the mixture was reacted under reflux and agitation for 10 hours. The reaction liquid was poured into diluted hydrochloric acid and the mixture was extracted with benzene. The extract was washed with an aqueous solution of edible salt and dried over Glauber's salt. The solvents were distilled off and the residue was distilled under reduced pressure to obtain 22.0 g (66.8%) of 4-octyloxybromobenzene.

GLC 99.8% b.p. 124°–127° C./0.2 mmHg (e) Synthesis of

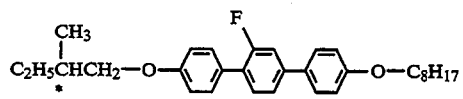

A reaction vessel was charged with 0.4 g of magnesium powder and a small piece of iodine. A small portion of a solution of 3.4 g of 4-octyloxybromobenzene obtained in (d) above in 20 ml of THF was added to and brought into reaction with the mixture. The remainder of the THF solution was then added dropwise with stirring while keeping the resultant mixture under reflux, and the mixture was refluxed with stirring for a further period of 2 hours to prepare a Grignard reagent.

Another reaction vessel was charged successively with 0.1 g of dichlorobistriphenylphosphinepalladium [Cl$_2$Pd(PPh$_3$)$_2$], 20 ml of THF, 0.5 ml of a 1M solution of diisobutylaluminum hydride [(iso-C$_4$H$_9$)$_2$AlH] in hexane and a solution of 2 g of (S)-4-(2-methylbutyl)oxy-2'-fluoro-4'-bromobiphenyl obtained in (c) above in 20 ml of THF under a nitrogen stream. The previously prepared Grignard reagent was added dropwise to the mixture with stirring at 50° C. After the dropwise addition, the mixture was reacted at the same temperature with stirring for 6 hours. The reaction liquid was poured into diluted hydrochloric acid and the mixture was extracted with benzene. The extract was washed with an aqueous solution of edible salt and dried over Glauber's salt. The solvents were distilled off and the residue was purified by way of column chromatography on silica gel using hexane:benzene (=6:1) as eluent, and then recrystallized from acetone, whereby 1.62 g (59.1%) of (S)-4-(2-methylbutyl)oxy-2'-fluoro-4''-octyloxy-p-terphenyl was obtained.

The purity of this product was at least 99% by HPLC. The thus obtained substance was confirmed to be the end product in view of its measurement by IR and its molecular ion peak found at 462 by Mass and in view of the starting materials used.

This product was inserted into a Mettler hot stage FP-82 and its phase transition was observed under a polarization microscope. A result of the observation is shown in Table 1.

EXAMPLE 5

(a) Synthesis of

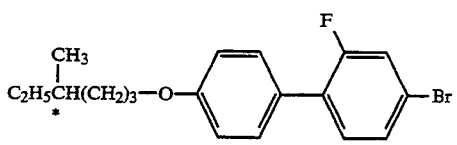

Except that 4.0 g of (S)-4-methylhexyl bromide was used in place of 6.8 g of (S)-2-methylbutyl bromide used in Example 4 (c), the operation was performed in the same manner as in Example 4 to obtain 4.47 g (65.4%) of (S)-4-(4-methylhexyl)oxy-2'-fluoro-4'-bromobiphenyl (GTO-set temperature: 165° C./0.25 mmHg).

TLC monospot (b) Synthesis of

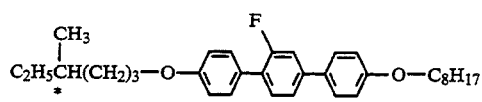

Except that (S) -4-(4-methylhexyl)oxy-2'-fluoro-4'-bromobiphenyl obtained in (a) above was used in place of (S)-4-(2-methylbutyl)oxy-2'-fluoro-4'-bromobiphenyl used in Example 4 (e), the operation was performed in the same manner as in Example 4 to obtain 1.06 g (39.5%) of (S)-4-(4-methylhexyl)oxy-2'-fluoro-4''-octyloxy-p-terphenyl.

The purity of this product was at least 99% by HPLC. The thus obtained substance was confirmed to be the end product in view of its measurement by IR and its molecular ion peak found at 490 by Mass and in view of the starting materials used.

This product was inserted into a Mettler hot stage FP-82 and its phase transition was observed under a polarization microscope. A result of the observation is shown in Table 1.

EXAMPLE 6

(a) Synthesis of

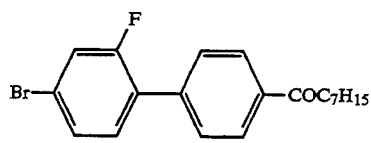

A reaction vessel was charged with 20 ml of methylene chloride and 3.2 g of anhydrous aluminum chloride. To the mixture was added 4 g of octanoyl chloride with stirring at a temperature not higher than −5° C. and was then added dropwise a solution of 3 g of 4-bromo-2-fluorobiphenyl in 10 ml of methylene chloride.

After the dropwise addition, the mixture was reacted for 3 hours with stirring at a temperature not higher than 0° C. and then allowed to stand overnight at room temperature. The reaction liquid was poured into ice/-diluted hydrochloric acid and the mixture was extracted with benzene. The benzene solution was washed with water, treated with diluted aqueous ammonia, washed with water and then dried over Glauber's salt. The benzene was distilled off and the residue was re-crystallized from acetone to obtain 3.8 g (84.2%) of 4-octanoyl-2'-fluoro-4'-bromobiphenyl.

TLC monospot (b) Synthesis of

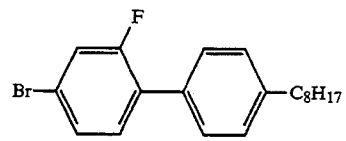

A reaction vessel was charged with 3.75 g of 4-octanoyl-2'-fluoro-4'-bromobiphenyl and 20 ml of trifluoroacetic acid. To the mixture was added dropwise 2.4 g of triethylsilane with stirring at room temperature. After stirring for 6 hours, the reaction liquid was poured into water and the mixture was extracted with benzene. The benzene extract was washed successively with water, an aqueous solution of sodium hydrogen carbonate and water, and then dried over Glauber's salt. The solvents were distilled off and the residue was distilled in a glass tube oven (GTO) to obtain 2.56 g (71.1%) of 4-octyl-2'-fluoro-4'-bromobiphenyl. GTO-set temperature: 150° C./0.2 mmHg.

TLC monospot (c) Synthesis of

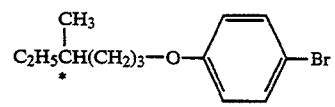

Except that 20.7 g of (S)-4-methylhexyl bromide was used in place of 22.3 g of octyl bromide used in Example 4 (d), the operation was performed in the same manner as in Example 4 to obtain 24.1 g (77%) of (S) -4-(4-methylhexyl)oxybromobenzene.

b.p. 120°–123° C./0.5 mmHg (d) Synthesis of

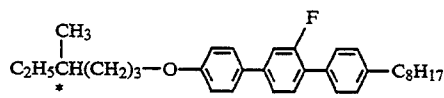

A reaction vessel was charged with 0.2 g of magnesium powder and a small piece of iodine. A small portion of a solution of 1.3 g of (S)-4-(4-methylhexyl)oxybromobenzene obtained in (c) above in 10 ml of THF was added to and brought into reaction with the mixture. The remainder of the THF solution was added dropwise thereto with stirring in such a manner that the resultant mixture was kept refluxed. The mixture was stirred under reflux for a further period of 2 hours to prepare a Grignard reagent. Another reaction vessel was charged successively with 0.1 g of dichlorobistriphenylphosphinepalladium [Cl₂Pd(PPh₃)₂], 10 ml of THF, 0.5 ml of a 1M solution of diisobutyl aluminum hydride [(iso-C₄H₉)₂AlH] in hexane and a solution of 1.7 g of 4-octyl-2'-fluoro-4'-bromobiphenyl obtained in (b) above in 10 ml of THF under a stream of nitrogen. To the mixture was added dropwise the previously prepared Grignard reagent with stirring at 50° C. After the dropwise addition, the mixture was reacted with stirring at the same temperature for 6 hours. The reaction liquid was poured into diluted hydrochloric acid and the mixture was extracted with benzene. The extract was washed with an aqueous solution of edible salt and dried over Glauber's salt. The solvents were distilled off and the residue was purified by column chromatography on silica gel (eluent:hexane:benzene=6:1) and then recrystallized from acetone to obtain 0.32 g (14.5%) of (S)-4-(4-methylhexyl)oxy-3'-fluoro-4"-octyl-p-terphenyl.

The purity of this product was at least 99% by HPLC. The thus obtained substance was confirmed to be the end product in view of its measurement by IR and its molecular ion peak found at 474 by Mass, and in view of the starting materials used.

This product was inserted into a Mettler hot stage FP-82 and its phase transition was observed under a polarization microscope. A result of the observation is shown in Table 1.

EXAMPLE 7

(a) Synthesis of

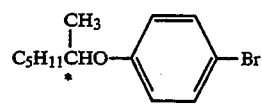

A reaction vessel was charged with 10 g of p-bromophenol, 19 g of (S)-1-methylhexyl tosylate, 10 g of potassium carbonate and 150 ml of cyclohexanone, and the mixture was stirred under reflux for 15 hours (the starting materials were confirmed to have disappeared by GLC). The reaction liquid was filtered and the filter cake was washed with benzen. The washings and the filtrate were combined, washed with water and then dried over Glauber's salt. The solvents were distilled off and the residue was purified by way of column chromatography on silica gel (eluent:hexane) to obtain 14 g (89.4%) of (R)-4-(1-methylhexyl)oxybromobenzene.

GLC 98.4%

(b) Synthesis of

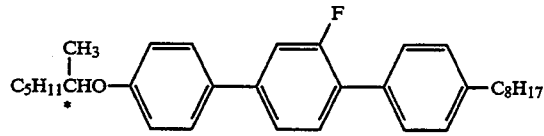

Except that 3.2 g of (R) -4- (1-methylhexyl )oxybromobenzene obtained in (a) above and 2.2 g of 4-octyl-2'-fluoro-4'bromobiphenyl obtained in Example 6 (b) were used in place of 3.4 g of 4-octyloxybromobenzene and 2 g of (S)-4-(2-methylbutyl)oxy-2'-fluoro-4'-bromobiphenyl used in Example 4 (e), respectively, the operation was performed in the same manner as in Example 4 to obtain 0.31 g (11%) of (R)-4-(1-methylhexyl)oxy-3'-fluoro-4'-octyl-p-terphenyl.

The purity of this product was at least 98% by HPLC. The thus obtained substance was confirmed to be the end product in view of its measurement by IR and its molecular ion peak found at 474 by Mass and in view of the starting materials used.

This product was inserted into a Mettler hot stage FP-82 and its phase transition was observed under a polarization microscope. A result of the observation is shown in Table 1.

EXAMPLE 8

(a) Synthesis of

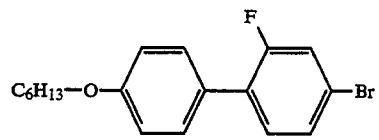

Except that 6 g of hexyl bromide was used in place of 6.8 g of (S)-2-methylbutyl bromide used in Example 4 (c), the operation was performed and after-treated in the same manner as in Example 4, and the resultant crude product was distilled in a glass tube oven (GTO) to obtain 5.8 g (88.3%)-of 4-hexyloxy-2'-fluoro-4'-bromobiphenyl. GTO-set temperature: 150° C./0.15 mmHg.

(b) Synthesis of

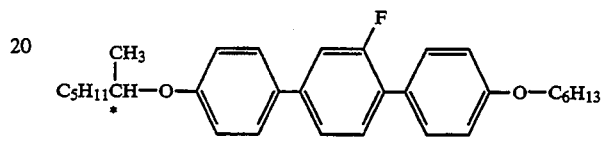

Except that 3 g of (R)-4-(1-methylhexyl)oxybromobenzene obtained in Example 7 (a) and 2 g of 4-hexyloxy-2'-fluoro-4'bromobiphenyl obtained in (a) above were used in place of 3.4 g of 4-octyloxybromobenzene and 2 g of (S)-4-(2-methylbutyl)oxy-2'-fluoro-4'-bromobiphenyl used in Example 4 (e), respectively, the operation was performed in the same manner as in Example 4 to obtain 0.4 g (15%) of (R)-4-(1-methylhexyl)oxy-3'-fluoro-4'-hexyloxy-p-terphenyl.

The purity of this product was at least 99% by HPLC. The resultant substance was confirmed to be the end product in view of its measurement by IR and its molecular ion peak found at 462 by Mass and in view of the starting materials used.

This product was inserted into a Mettler hot stage FP-82 and its phase transition was observed under a polarization microscope. A result of the observation is shown in Table 1.

EXAMPLE 9

(a) Synthesis of

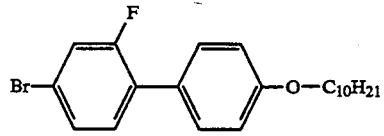

A reaction vessel was charged with 12 g of 4-hydroxy-2'-fluoro-4'-bromobiphenyl obtained in Example 4(b), 14.2 g of decyl bromide, 15.7 g of potassium carbonate and 100 ml of 2-butanone (MEK), and the mixture was refluxed with stirring for 12 hours (the disappearance of the starting materials were confirmed by TLC). The reaction liquid was poured into diluted hydrochloric acid and the mixture was extracted with benzene. The extract was washed with water and dried over Glauber's salt. The solvents were distilled off and the residue was purified by way of column chromatography on silica gel (eluent:hexane) and then recrystallized from hexane to obtain 14.9 g (81.5%) of 4-decyloxy-2'-fluoro-4'-bromobiphenyl.

(b) Synthesis of

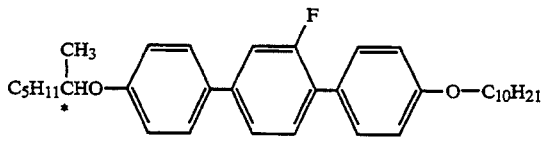

Except that 2.4 g of 4-decyloxy-2'-fluoro-4'-bromobiphenyl obtained in (a) was used in place of 2.2 g of 4-octyl-2'-fluoro-4'-bromobiphenyl used in Example 7 (b), the operation was performed in the same manner as in Example 7 to obtain 0.55 g (18%) of (R)-4-(1-methylhexyl)oxy-3'-fluoro-4"-decyloxy-p-terphenyl.

The purity of this product was at least 98% by HPLC. The resultant substance was confirmed to be the end product in view of its measurement by IR and its molecular ion peak found at 518 by Mass and in view of the starting materials used.

This product was inserted into a Mettler hot stage FP-82 and its phase transition was observed under a polarization microscope. A result of the observation is shown in Table 1.

EXAMPLE 10

(a) Synthesis of

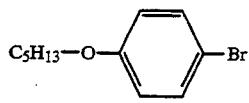

Except that 19 g of hexyl bromide was used in place of 22.3 g of octyl bromide used in Example 4 (d), the operation was performed in the same manner as in Example 4 to obtain 26.7 g (89.9%) of 4-hexyloxybromobenzene.

b.p. 106°–115° C./0.5 mmHg (b) Synthesis of

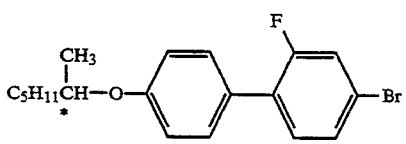

Except that 7.5 g of (R)-1-methylhexyl tosylate was used in place of 6.8 g of (S)-2-methylbutyl bromide used in Example 4 (c), the operation and aftertreatment were performed in the same manner as in Example 4, and the resultant crude product was purified by way of column chromatography on silica gel (eluent:hexane) to obtain 6.1 g (89.3%) of (S)-4-(1-methylhexyl)oxy-2'-fluoro-4'-bromobiphenyl.

(c) Synthesis of

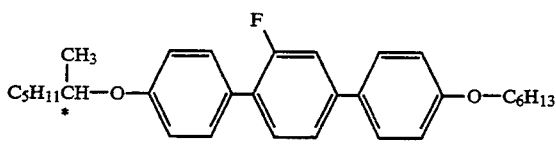

Except that 3 g of 4-hexyloxybromobenzene obtained in (a) above and 2.0 g of (S) -4-(1-methylhexyl)oxy-2'-fluoro-4'-bromobiphenyl obtained in (b) above were used in place of 3.4 g of 4-octyloxybromobenzene and 2.0 g of (S)-4-(2-methylbutyl)oxy-2'-fluoro-4'-bromobiphenyl used in Example 4 (e), respectively, the operation was performed in the same manner as in Example 4 to obtain 0.25 g (10%) of (S)-4-(1-methylhexyl)oxy-2'-fluoro-4'-hexyloxy-p-terphenyl.

The purity of this product was at least 99% by HPLC. The resultant substance was confirmed to be the end product in view of its measurement by IR and its molecular ion peak found at 462 by Mass and in view of the starting materials used.

This product was inserted into a Mettler hot stage FP-82 and its phase transition was observed under a polarization microscope. A result of the observation is shown in Table 1.

EXAMPLE 11

(a) Synthesis of

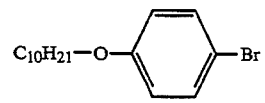

Except that 25.7 g of decyl bromide was used in place of 22.3 g of octyl bromide used in Example 4 (d), the operation was performed in the same manner as in Example 4 to obtain 31.0 g (85.8%) of 4-decyloxybromobenzene.

b.p. 136°–146° C./0.25 mmHg (b) Synthesis of

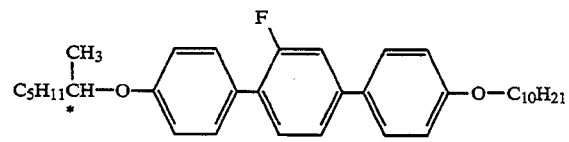

Except that 3.5 g of 4-decyloxybromobenzene obtained in (a) above and 2.0 g of (S)-4-(1-methylhexyl)oxy-2'-fluoro-4'-bromobiphenyl obtained in Example 10 (b) were used in place of 3.4 g of 4-octyloxybromobenzene and 2 g of (S)-4-(2-methylbutyl)oxy-2'-fluoro-4'-bromobiphenyl used in Example 4 (e), respectively, the operation was performed in the same manner as in Example 4 to obtain 0.42 g (14.8%) of (S)-4-(1-methylhexyl)oxy-2'-fluoro-4"-decyloxy-p-terphenyl.

The purity of this product was at least 99% by HPLC. The resultant substance was confirmed to be the end product in view of its measurement by IR and its molecular ion peak found at 518 by Mass and in view of the starting materials used.

This product was inserted into a Mettler hot stage FP-82 and its phase transition was observed under a polarization microscope. A result of the observation is shown in Table 1.

EXAMPLE 12

(a) Synthesis of

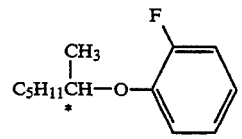

A reaction vessel was charged with 10 g of 2-fluorophenol, 25 g of (S)-1-methylhexyl tosylate, 20 g of potassium carbonate and 160 ml of MEK, and the mixture was refluxed with stirring for 14 hours (the disappearance of the starting materials was confirmed by TLC). The reaction liquid was poured into diluted hydrochloric acid and the mixture was extracted with benzene. The extract was washed with water and dried over Glauber's salt, and the solvents were distilled off. The residue was distilled under reduced pressure to obtain 14 g (74.5%) of (R)-2-(1-methylhexyl)oxyfluorobenzene.

b.p. 113°-117° C./9 mmHg (b) Synthesis of

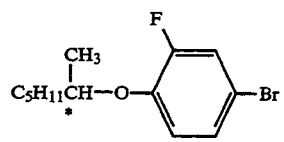

A reaction vessel was charged with 13.9 g of (R)-2-(1-methylhexyl)oxyfluorobenzene obtained in (a) above and 50 ml of chloroform. To the mixture was added dropwise 12.7 g of bromine with stirring at room temperature. The resultant mixture was further stirred at room temperature (until the starting materials were confirmed by GLC to have disappeared) and a 10 % aqueous solution of caustic soda was added with stirring. The organic layer was washed with water and dried over Glauber's salt. The solvents were distilled off and the residue was distilled under reduced pressure to obtain 14.2 g (74.1%) of (R)-4-(1-methylhexyl)oxy-3-fluorobromobenzene.

b.p. 98°-110° C./0.3 mmHg (c) Synthesis of

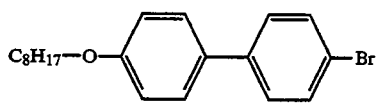

A reaction vessel was charged with 15 g of 4-hydroxy-4'-bromobiphenyl, 14 g of octyl bromide, 16 g of potassium carbonate and 100 ml of MEK, and the mixture was refluxed with stirring for 8 hours (the disappearance of the starting materials was confirmed by GLC). The reaction liquid was filtered to remove solids. The filtrate was concentrated and the residue was recrystallized from acetone to obtain 18 g (90%) of 4-octyloxy-4'-bromobiphenyl.

(d) Synthesis of

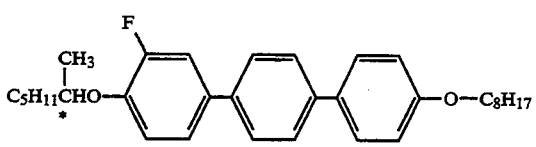

Except that 4.3 g of 4-octyloxy-4'-bromobiphenyl obtained in (c) above and 1.7 g of (R)-4-(1-methylhexyl)oxy-3-fluorobromobenzene obtained in (b) above were used in place of 3.4 g of 4-octyloxybromobenzene and 2.0 g of (S)-4-(2-methylbutyl)oxy-2'-fluoro-4'-bromobiphenyl used in Example 4 (e), respectively, the operation was performed in the same manner as in Example 4 to obtain 0.47 g (16%) of (R)-4-(1-methylhexyl)oxy-3-fluoro-4 '-octyloxy-p-terphenyl.

The purity of this product was at least 99% by HPLC. The resultant substance was confirmed to be the end product in view of its measurement by IR and its molecular ion peak found at 490 by Mass and in view of the starting materials used.

This product was inserted into a Mettler hot stage FP-82 and its phase transition was observed under a polarization microscope. A result of the observation is shown in Table 1.

EXAMPLE 13

Synthesis of

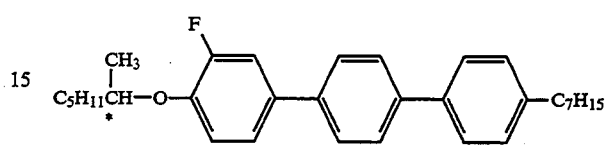

Except that 3.9 g of 4-heptyl-4'-bromobiphenyl was used in place of 4.3 g of 4-octyloxy-4'-bromobiphenyl used in Example 12 (d), the operation was performed in the same manner as in Example 12 to obtain 1.7 g (62.1%) of (R)-4-(1-methylhexyl)oxy-3-fluoro-4''-heptyl-p-terphenyl.

The purity of this product was at least 99% by HPLC. The resultant substance was confirmed to be the end product in view of its measurement by IR and its molecular ion peak found at 460 by Mass and in view of the starting materials used. This product was inserted into a Mettler hot stage FP-82 and its phase transition was observed under a polarization microscope. A result of the observation is shown in Table 1.

EXAMPLE 14

(a) Synthesis of

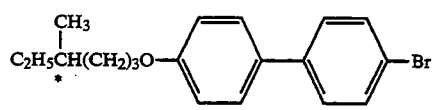

A reaction vessel was charged with 1.1 g of 4-hydroxy-4'-bromobiphenyl, 20 ml of 2-butanone, 1.2 g of potassium carbonate and 0.95 g of (S)-4-methylhexyl bromide, and the mixture was refluxed with stirring until TLC showed the disappearance of the starting materials. It took 10 hours for this. The reaction liquid was filtered to remove solids and the filtrate was concentrated. The residue was dried under reduced pressure to obtain 1.4 g (93%) of (S)-4-(4-methylhexyl)oxy-4'-bromobiphenyl.

GLC 96%

(b) Synthesis of

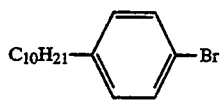

Except that 4-decylaniline was used in place of 4-pentylaniline used in Example 1 (a), the operation was performed in the same manner as in Example 1 to obtain 48.4 g (38%) of 4-decylbromobenzene.

b.p. 136°-141° C./0.4 mmHg (c) Synthesis of

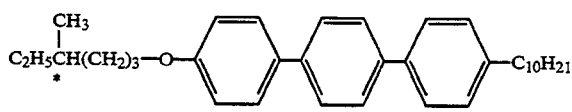

A reaction vessel was charged with 0.35 g of magnesium powder and a small piece of iodine. To this mixture was added a small portion of a solution of 4 g of 4-decylbromobenzene obtained in (b) above in 10 ml of THF, whereupon foaming occurred to initiate the reaction. The remainder of the THF solution mentioned above was then added dropwise with stirring in such a manner that the resultant mixture was kept refluxed. After the dropwise addition, the mixture was refluxed with stirring for 2 hours to prepare a Grignard reagent. Another reaction vessel was charged with 50 mg of dichlorobistriphenylphosphinepalladium [$Cl_2Pd(PPh_3)_2$] and 3 ml of THF. To this mixture was added 0.1 ml of a 1M solution of diisobutylaluminum hydride [(iso-$C_4H_9$)$_2$AlH] in hexane. A solution of 1.4 g of (S)-4-(4-methylhexyl)oxy-4'-bromobiphenyl obtained in (a) above in 5 ml of THF was then added. After the temperature of the mixture rose to 60° C., the previously prepared Grignard reagent was added dropwise. After the dropwise addition, the mixture was allowed to ripe for 2 hours. The reaction liquid was poured into ice-cooled diluted hydrochloric acid and the mixture was extracted with benzene. The extract was washed with a saturated aqueous solution of edible salt until the washings became neutral, and then dried over Glauber's salt. The solvents were distilled off and the residue was treated with hexane. Hexane-insolubles were recrystallized from acetone to obtain 0.2 g (11%) of (S)-4-(4-methylhexyl)oxy-4''-decyl-p-terphenyl.

The purity of this product was at least 99% by HPLC. The resultant substance was confirmed to be the end product in view of its measurement by IR and its molecular ion peak found at 484 by Mass and in view of the starting materials used.

This product was inserted into a Mettler hot stage FP-82 and its phase transition was observed under a polarization microscope. A result of the observation is shown in Table 1.

EXAMPLE 15

Synthesis of

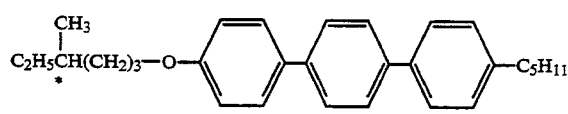

Except that 3.06 g of 4-pentylbromobenzene obtained in Example 1 (a) was used in place of 4 g of 4-decylbromobenzene used in Example 14 (c), the operation was performed in the same manner as in Example 14 to obtain 0.41 g (25%) of (S)-4-(4-methylhexyl)oxy-4''-pentyl-p-terphenyl.

The purity of this product was at least 98% by HPLC. The resultant was confirmed to be the end product in view of its measurement by IR and its molecular ion peak found at 414 by Mass and in view of the starting materials used.

This product was inserted into a Mettler hot stage FP-82 and its phase transition was observed under a polarization microscope. A result of the observation is shown in Table 1.

EXAMPLE 16

(a) Synthesis of

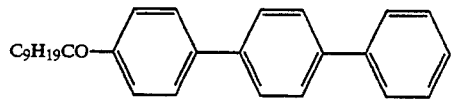

A reaction vessel was charged with 5.7 g of p-terphenyl and 40 ml of methylene chloride. To this mixture was added 4 g of anhydrous aluminum chloride with stirring at 0° C. A solution of 5.2 g of decanoyl chloride in 10 ml of methylene chloride was added dropwise. After the dropwise addition, the mixture was stirred for 5 hours. The reaction liquid was poured into diluted hydrochloric acid and the mixture was stirred well. Insolubles were collected by filtration, washed and dried to obtain 6.8 g (71%) of 4-decanoyl-p-terphenyl.

HPLC 93.3%

(b) Synthesis of

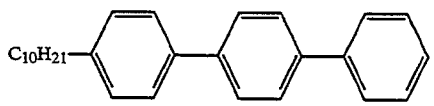

A reaction vessel was charged with 6.8 g of 4-decanoyl-p-terphenyl obtained in (a) above, 50 ml of diethylene glycol, 3.4 g of 80% hydrazine hydrate and a solution of 1.8 g of 88% caustic potash in 4 ml of water. The reaction was carried out with stirring at 130° C. for 5 hours and, after having raised the temperature while distilling off the water, at 210° C. for 3 hours (the disappearance of the starting materials was confirmed by TLC). The reaction liquid was poured into diluted hydrochloric acid and the mixture was extracted with benzene. The extract was washed with water and dried over Glauber's salt. The solvents were distilled off and the residue was recrystallized from THF to obtain 5.1 g (77.6%) of 4-decyl-p-terphenyl.

HPLC 97.3%

(c) Synthesis of

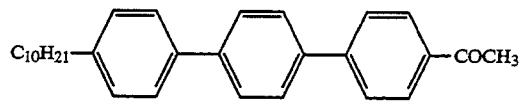

A reaction vessel was charged with 5 g of 4-decyl-p-terphenyl obtained in (b) above and 30 ml of methylene chloride. To this mixture was added 2.2 g of anhydrous aluminum chloride with stirring at 0° C., and was then added a solution of 1.3 g of acetyl chloride in 10 ml of methylene chloride. After the dropwise addition, the reaction was carried out with stirring at the same temperature until the disappearance of the starting materials (confirmed by TLC). It took 6 hours for this. The reaction liquid was poured into ice/diluted hydrochloric acid, and the precipitate was collected by filtration and washed with water. This product and the residue, obtained by distilling off the solvent from the methylene chloride layer of the filtrate after the layer was washed with water and dried over Glauber's salt, were combined and recrystallized from THF to obtain 4.4 g (78%) of 4-acetyl-4''-decyl-p-terphenyl.
HPLC 99.4%
(d) Synthesis of

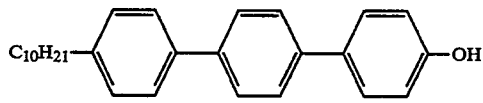

A reaction vessel was charged with 2 g of 4-acetyl-4''-decyl-p-terphenyl obtained in (c) above and 20 ml of methylene chloride. To this mixture were added with stirring at room temperature 8 g of 88% formic acid, 3 g of acetic anhydride and 1 ml of concentrated sulfuric acid, successively, and was then added dropwise at 14° C. 3 g of 35% aqueous hydrogen peroxide. After the dropwise addition, the reaction was carried out at 40° C. with stirring until TLC showed the disappearance of the starting materials, while adding 35% aqueous hydrogen peroxide as appropriate. The reaction liquid was poured into ice/water and the methylene chloride layer was separated and dried over Glauber's salt. The solvent was distilled off to obtain 4 g of the residue (4-acetyloxy-4''-decyl-p-terphenyl). A reaction vessel was charged with 4 g of this residue, 150 ml of ethanol and a solution of 1 g of 85% caustic potash in 2 ml of water. The mixture was refluxed with stirring for 13 hours. The reaction liquid was poured into water and the mixture was acidified with hydrochloric acid and extracted with ether. The extract was washed with water and dried over Glauber's salt. The solvent was distilled off and the residue was recrystallized from hexane to obtain 1.2 g (63%) of 4-hydroxy-4''-decyl-p-terphenyl.
(e) Synthesis of

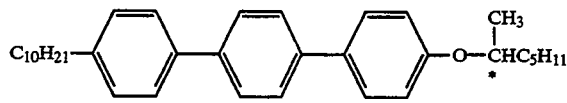

A reaction vessel was charged with 0.4 g of 4-hydroxy-4''-decyl-p-terphenyl obtained in (d) above, 20 ml of 2-butanone, 0.2 g of potassium carbonate and 0.35 g of (S)-1-methylhexyl tosylate, and the mixture was refluxed with stirring for 17 hours. The reaction liquid was filtered with suction to remove solids and the filtrate was concentrated. The residue was purified by way of column chromatography on silica gel (hexane/benzene=5:1) to obtain 0.13 g (27%) of (R)-4-(1-methylhexyl)oxy-4''-decyl-p-terphenyl.

The purity of this product was at least 99% by HPLC. The resultant substance was confirmed to be the end product in view of its measurement by IR, and its molecular ion peak found at 484 by Mass and in view of the starting materials used.

This product was inserted into a Mettler hot stage FP-82 and its phase transition was observed under a polarization microscope. A result of the observation is shown in Table 1.

EXAMPLE 17

(a) Synthesis of

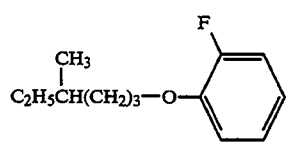

Except that 17 g of racemic-4-methylhexyl bromide was used in place of 25 g of (S)-1-methylhexyl tosylate used in Example 12 (a), the operation was performed in the same manner as in Example 12 (a) to obtain 15 g (80%) of racemic-2-(4-methylhexyl)oxyfluorobenzene.
b.p. 120°–122° C./7 mmHg
(b) Synthesis of

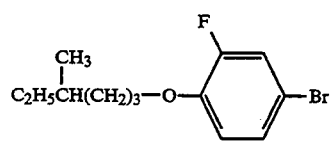

Except that 13.9 g of racemic-2-(4-methylhexyl)-oxyfluorobenzene obtained in (a) above was used in place of 13.9 g of (R)-2-(1-methylhexyl)oxyfluorobenzene used in Example 12 (b), the operation was performed in the same manner as in Example 12 (b) to obtain 16.7 g (87%) of racemic-4-(4-methylhexyl)oxy-3-fluorobromobenzene.
b.p. 124°–130° C./0.25 mmHg
(c) Synthesis of

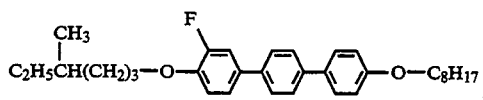

Except that 3.4 g of racemic-4-(4-methylhexyl)oxy-3-fluorobromobenzene obtained in (b) above and 2.1 g of 4'-octyloxy-4-bromobiphenyl obtained in Example 12 (c) were used in place of 3.4 g of 4-octyloxy-bromobenzene and 2.0 g of (S)-4-(2-methylbutyl)oxy-2'-fluoro-4'-bromobiphenyl used in Example 4(e), respectively, the operation was performed in the same manner as in Example 4 (e) to obtain 0.87 g (30%) of racemic-4-(4-methylhexyl)oxy-3-fluoro-4''-octyloxy-p-terphenyl.

The purity of this product was at least 99% by HPLC. The resultant substance was confirmed to be the end product in view of its measurement by IR and its molecular ion peak found at 490 by Mass and in view of the starting materials used. This product was inserted into a Mettler hot stage FP-82 and its phase transition was observed under a polarization microscope. A result of the observation is shown in Table 2.

EXAMPLE 18

(a) Synthesis of

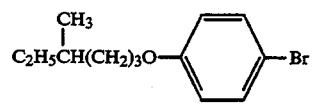

Except that 20.8 g of racemic-4-methylhexyl bromide was used in place of 22.3 g of octyl bromide used in Example 4 (d), the operation was performed in the same manner as in Example 4 (d) to obtain 18 g (58%) of racemic-4-(4-methylhexyl)-oxybromobenzene.

b.p. 109°–115° C./mmHg GLC at least 99%
(b) Synthesis of

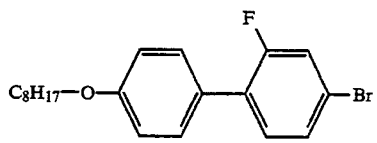

Except that 5.2 g of octyl bromide was used in place of 6.8 g of (S)-2-methylbutylbromide used in Example 4 (c), the operation as well as the after treatment was performed in the same manner as in Example 4 (c). The resultant crude product was purified by way of column chromatography on silica gel (eluent:hexane) to obtain 6.3 g (88.7%) of 4-octyloxy-2'-fluoro-4'-bromobiphenyl.
(c) Synthesis of

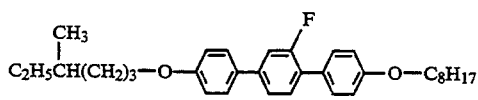

Except that 3.2 g of racemic-4-(4-methylhexyl)-oxy-bromobenzene obtained in (a) above and 2.2 g of 4-octyloxy-2'-fluoro-4'-bromobiphenyl obtained in (b) above were used in place of 3.4 g of 4-octyloxybromobenzene and 2.0 g of (S)-4-(2-methylbutyl)oxy-2'-fluoro-4'-bromobiphenyl used in Example 4 (e), respectively, the operation was performed in the same manner as in Example 4 (e) to obtain 0.29 g (10%) of racemic-4-(4-methylhexyl)oxy-3'-fluoro-4''-octyloxy-p-terphenyl.

The purity of this product was at least 99% by HPLC. The resultant substance was confirmed to be the end product in view of its measurement by IR and its molecular ion peak found at 490 by Mass and in view of the starting materials.

This product was inserted into a Mettler hot stage FP-82 and its phase transition was observed under a polarization microscope. A result of the observation is shown in Table 2.

TABLE 1

| Example No. | C | Sx1 | Sx2 | SB | SC* | SA | Ch | I |
|---|---|---|---|---|---|---|---|---|
| 1 | • ? | • | | • 61.5 | | • 106.5 | • 120.5 | • |
| 2 | • ? | • 43.5 | | | • 112.5 | • 122 | • 139.5 | • |
| 3 | • ? | | | | | • 62.5 | | • |
| | | | | Sx3 | | | | |
| 4 | • 52.5 | • 66.5 | • 77.5 | • 94.5 | • 145 | • 154.5 | | • |
| 5 | • 90 | • 97 | | | • 158 | • 161 | • 162.5 | • |
| 6 | • 49.5 | • 57 | | | • 122 | • 127.5 | • 130.5 | • |
| 7 | • 37 | | | | (• 17) | (• 28) | | • |
| 8 | • 71 | | | | • 72.3 | • 99.5 | | • |
| 9 | • 77 | | | | • 83.5 | • 96.5 | | • |
| 10 | • 77 | | | • 90 | | • 117 | | • |
| 11 | • 89 | | | | • 106 | • 111.5 | | • |
| 12 | • 121.5 | | | | • 135 | • 148 | | • |
| 13 | • ? | • 66.5 | | • 90.5 | | • 122 | | • |
| 14 | • 65 | • 181.5 | | | • 188.5 | • 191 | | • |
| 15 | • ? | | | • 198 | | • 215.5 | | • |
| 16 | • 76.5 | • 101.5 | • 116 | | • 122.5 | • 126 | | • |

TABLE 2

| Example No. | C | Sx1 | Sx2 | SB | SC | SA | Ne | I |
|---|---|---|---|---|---|---|---|---|
| 17 | • 175.5 | | | | • 197.0 | • 199.5 | | • |
| 18 | • 93.5 | | | | | • 151.5 | • 162 | • |

EXAMPLE 19

A 3 μm-thick liquid crystalline cell, provided with transparent electrodes, was prepared by subjecting the polyvinyl alcohol (PVA)-coated-surface to a parallel aligning treatment by rubbing. One of the compounds obtained in Examples was mixed with the following pyridine-type liquid crystalline composition in a ratio of 10:90 by weight. The thus prepared new liquid crystalline composition was enclosed in the liquid crystalline cell and gradually cooled from the isotopic liquid phase to SmC* phase to prepare a liquid crystal element. This liquid crystal element was interposed between two polarization panels and a 200 Hz square wave of ±25 V was applied thereto. Response times were determined from changes in intensity of transmission light. The results are shown below.

Pyrimidine-type liquid crystalline composition used:

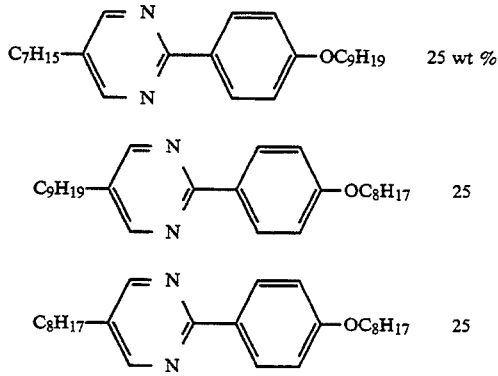

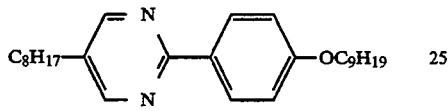

The temperature range for the SmC* phase found upon cooling, of this liquid crystalline composition was 54°–12° C.

| Compound of the invention added | Response time (μsec) | Measurement temperature (°C.) | SmC* temperature range upon cooling (°C.) |
|---|---|---|---|
| Example 3 | 256 | 40 | 43–3 |
| Example 7 | 284 | 42 | 45–1 |
| Example 9 | 348 | 52 | 55–4 |
| Example 13 | 230 | 47 | 50–1 |
| Example 16 | 295 | 48 | 51–1 |

As is apparent from the above, the compounds of the present invention are useful substances utilizable for the manufacture of practical, ferroelectric liquid crystal display elements.

What is claimed is:

1. A p-terphenyl derivative of the formula

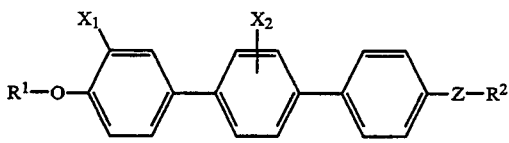

wherein $R^1$ represents a group of the formula —CH$_2$—R wherein R is an asymetric carbon-containing alkyl group having 3–17 carbon atoms; $R^2$ is a straight chain alkyl group having 5–18 carbon atoms; Z is a single bond, O, COO or OCO; and one of $X_1$ and $X_2$ is a hydrogen atom, and the other is a fluorine atom, $X_2$ being in the 2' or 3' position in case of a fluorine atom; wherein said derivative exhibits a chiral smetic C phase.

2. The p-terphenyl derivative according to claim 1 which has the structure:

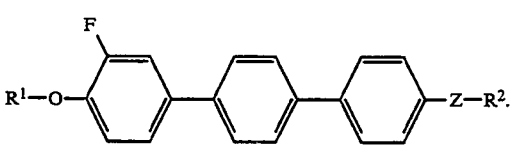

3. The p-terphenyl derivative according to claim 1 which has the structure:

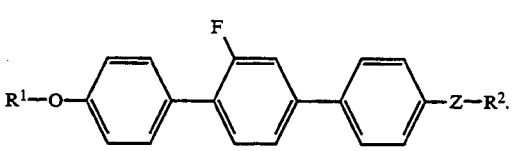

4. The p-terphenyl derivative according to claim 1 which has the structure:

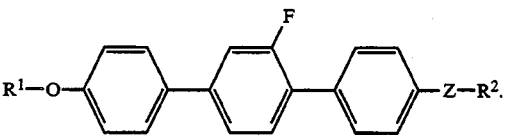

5. The p-terphenyl derivative according to claim 1, wherein said derivative exhibits a chiral smetic C phase over at least a 50° C. temperature range.

6. The p-terphenyl derivative according to claim 1, wherein the total number of carbon atoms contained in group $R^1$ and $R^2$ is at least 11.

7. The p-terphenyl derivative according to claim 1, wherein $X_1$ is hydrogen, $R^1$ is C$_2$H$_5$CH(CH$_3$)(CH$_2$)$_3$—.

8. The p-terphenyl derivative according to claim 1, wherein $X_1$ is hydrogen, Z is O, and $R^1$ is C$_2$H$_5$CH(CH$_3$)CH$_2$— or C$_2$H$_5$CH(CH$_3$)(CH$_2$)$_3$—.

9. The p-terphenyl derivative according to claim 1, wherein said derivative is selected from the group consisting of

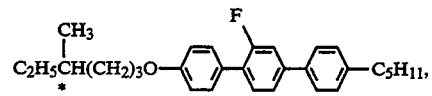

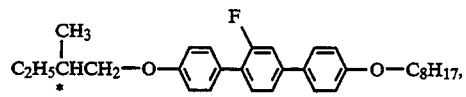

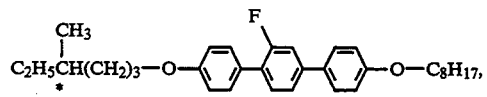

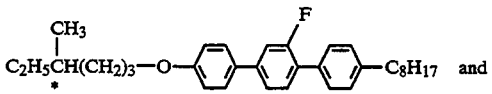 and

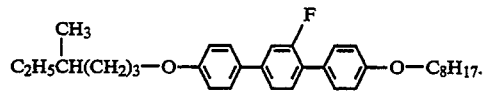

10. A ferroelectric liquid crystalline composition comprising at least one p-terphenyl derivative of the formula

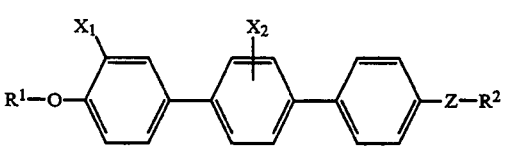

wherein $R^1$ represents a group of the formula —CH$_2$—R wherein R is an asymmetric carbon-containing alkyl group having 3–17 carbon atoms; $R^2$ is a straight chain alkyl group having 5–18 carbon atoms; Z is a single bond, O, COO or OCO; and one of $X_1$ and $X_2$ is a hydrogen atom, and the other is a fluorine atom, $X_2$ being in the 2' or 3' position in case of a fluorine atom; wherein said derivative exhibits a chiral smetic C phase and said composition exhibits a ferroelectric response.

11. The ferroelectric liquid crystalline composition according to claim 10, which further comprises at least one compound selected from the group consisting of

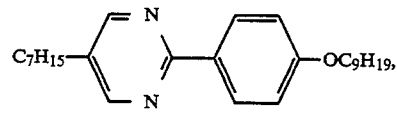

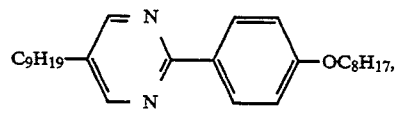

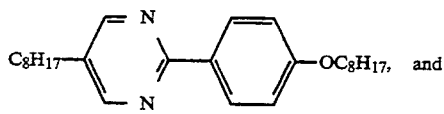

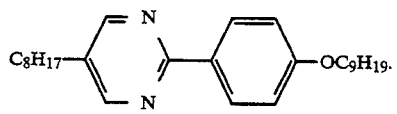

12. The ferroelectric liquid crystalline composition according to claim 10 wherein the p-terphenyl derivative has the structure:

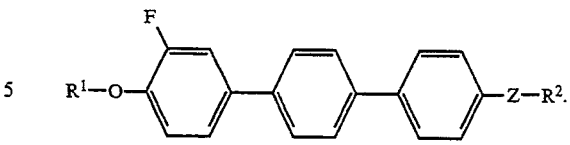

13. The ferroelectric liquid crystalline composition according to claim 10, wherein the p-terphenyl derivative has the structure:

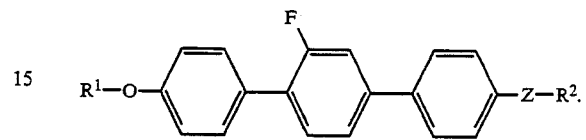

14. The ferroelectric liquid crystalline composition according to claim 10, wherein the p-terphenyl derivative has the structure:

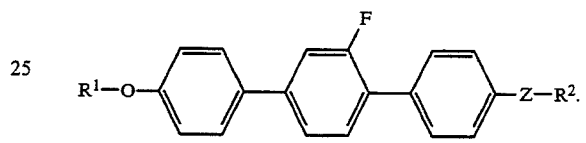

* * * * *